(12) United States Patent
Cela et al.

(10) Patent No.: US 9,155,879 B2
(45) Date of Patent: Oct. 13, 2015

(54) VIRTUAL ELECTRODES FOR HIGH-DENSITY ELECTRODE ARRAYS

(75) Inventors: Carlos J. Cela, Salt Lake City, UT (US); Gianluca Lazzi, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 13/440,925

(22) Filed: Apr. 5, 2012

(65) Prior Publication Data

US 2013/0041449 A1    Feb. 14, 2013

Related U.S. Application Data

(60) Provisional application No. 61/516,818, filed on Apr. 8, 2011.

(51) Int. Cl.
*A61N 1/05* (2006.01)
*A61N 1/36* (2006.01)

(52) U.S. Cl.
CPC ............ *A61N 1/0531* (2013.01); *A61N 1/0553* (2013.01); *A61N 1/36185* (2013.01)

(58) Field of Classification Search
CPC ............ A61N 1/0452; A61N 1/36185; A61N 1/0492; A61N 1/0531; A61N 1/0553
USPC ..................................... 607/2, 116, 148, 152
See application file for complete search history.

(56) References Cited

U.S. PATENT DOCUMENTS 7,987,000 B2 *   7/2011   Moffitt et al. ................. 607/117
8,433,403 B2 *   4/2013   Fahey ............................... 607/3

\* cited by examiner

*Primary Examiner* — Amanda Patton
(74) *Attorney, Agent, or Firm* — Norton Rose Fulbright US LLP

(57) ABSTRACT

The present embodiments are directed to implantable electrode arrays having virtual electrodes. The virtual electrodes may improve the resolution of the implantable electrode array without the burden of corresponding complexity of electronic circuitry and wiring. In a particular embodiment, a virtual electrode may include one or more passive elements to help steer current to a specific location between the active electrodes. For example, a passive element may be a metalized layer on a substrate that is adjacent to, but not directly connected to an active electrode. In certain embodiments, an active electrode may be directly coupled to a power source via a conductive connection. Beneficially, the passive elements may help to increase the overall resolution of the implantable array by providing additional stimulation points without requiring additional wiring or driver circuitry for the passive elements.

14 Claims, 15 Drawing Sheets

VIRTUAL ELECTRODES FOR HIGH-DENSITY ELECTRODE ARRAYS

CROSS-REFERENCE TO RELATED APPLICATIONS

This application claims priority to U.S. Provisional Patent Application No. 61/516,818, filed Apr. 8, 2011 and entitled, "VIRTUAL ELECTRODES," the entire contents of which are specifically incorporated herein by reference without disclaimer.

GOVERNMENT INTEREST

This invention was made with government support under DE-SC0004116 awarded by the Department of Energy. The government has certain rights in the invention.

TECHNICAL FIELD

This invention relates to bio-stimulation devices and more particularly relates to virtual electrodes for implantable bio-stimulation devices.

BACKGROUND

Electrical stimulator devices are used to stimulate various types of organic tissue. For example, electronics may be interfaced with the nervous system of a human body through use of neurostimulators. A neurostimulator is a device that may be implanted into human tissue, and provides stimulation to neurons through electrical pulses. For such reasons, neurostimulators may be referred to as implanted pulse generators (IPGs).

A typical neurostimulator includes one or more electrodes. Some neurostimulators include arrays of electrodes configured in implantable devices. For example, FIG. 1 illustrates a typical system 100 for neurostimulation. The system 100 includes an implantable electrode array 102 which may be implanted in organic tissue 106. For example, the implantable electrode array 102 may be implanted in a human brain or near optical or auditory nerves. The system 100 also includes a controller 104 coupled to the implantable electrode array 102. The electrode controller 104 is often located outside of the body. In certain systems, however, the electrode controller 104 may also be implantable.

FIG. 2 illustrates one configuration of a electrode array 102. As illustrated, the electrode array 102 includes a plurality of electrodes 202a-d, and a current return 204. A dielectric backing 107 mechanically supports the array and helps directing the charge injection into the tissue. The electrode array 102 may be implanted so the electrodes are in contact with organic tissue 106. In most prior systems, the current return 204 is placed in a region relatively distal from the electrode array 102. Each of the electrodes is coupled to a power source which injects charge on the electrodes 202a-d. The charge is injected through the organic tissue 106 to the current return 204, thus stimulating the organic tissue 106 between the electrodes 202a-d and the current return 204. Typically, only the portions of organic tissue 106 directly proximate each of the electrodes 202a-d are stimulated.

In order to increase the stimulation resolution of an electrode array 102, additional electrodes 202 may be included in the electrode array 102. For example, in the case of a retinal prosthesis, the electrode array 102 may originally have included nine electrodes 202. In an effort to increase resolution, the electrode array 102 could eventually include sixty-four electrodes 202 and then two hundred electrodes 202 or more in later versions.

In prior stimulator systems, as the number of electrodes increases, for the same size device, each electrode has to be smaller. This causes the current density at the vicinity of the stimulating electrodes to grow accordingly, to a point in which further miniaturization may lead to current density magnitudes that can damage the tissue. Additionally an additional wire and an additional driver circuit are typically required for each electrode, and the wire needs to have a large enough section to allow the appropriate amount of current to flow. These wires make the implant bulkier, mechanically stiffer, and in general harder to conform to delicate anatomical features.

SUMMARY

The present embodiments are directed to implantable electrode arrays having virtual electrodes. The virtual electrodes may improve the resolution of the implantable electrode array without the burden of corresponding additional wiring and complexity of electronic circuitry. In a particular embodiment, a virtual electrode may include one or more passive elements. For example, a passive element may be a metalized layer on a substrate that is adjacent to, but not directly connected to an active electrode. In certain embodiments, an active electrode may be directly coupled to a power source via a conductive connection. Beneficially, the passive elements may help to increase the overall resolution of the implantable array by providing additional stimulation points without requiring additional wiring or driver circuitry for the passive elements.

In the proposed scheme, the excitation waveform used in the electrodes has higher frequency components than what the body can react to. The neural cells being stimulated respond then to an averaged stimulus over time.

Embodiments of an apparatus for stimulating biological tissue are described. In one embodiment, the apparatus includes a first active electrode configured to receive a current from a current source and injecting it into organic tissue. The apparatus may also include a second active electrode configured to return current emitted by the first active electrode to ground. Additionally, the apparatus may include a region defining a virtual electrode disposed between the first active electrode and the second active electrode.

In further embodiments, a portion of the current emitted by the first active electrode is collected in the region defining the virtual electrode. Additionally, the time-average current density present in the region defining the virtual electrode is sufficient to stimulate biological tissue in proximate to the region defining the virtual electrode. The region defining the virtual electrode may include one or more passive elements. The passive elements may include a conductive layer disposed on a substrate in the region defining the virtual electrode. Additionally, an electrical insulation barrier may be disposed between the first and second active elements and the one or more passive elements. In one embodiment, the one or more passive elements are shaped in a pattern of a cross, a center point of the cross being disposed at a center point of the region defining the virtual electrode. In another embodiment, a majority portion of the region defining the virtual electrode comprises the one or more passive elements.

In such embodiments, the apparatus may include a plurality of active electrodes arranged in an array. Additionally, the apparatus may include a plurality of regions defining virtual electrodes, the virtual electrodes positioned between the plurality of active electrodes in the array. This is accomplished by means of tiling the same electrode pattern over a larger region.

Embodiments of systems for stimulating biological tissue are also presented. In one embodiment, the system includes an implantable bio-stimulator device. The implantable bio-stimulator device may have a first active electrode configured to inject current into tissue from a current source, a second active electrode configured to sink the current injected by the first active electrode, and a region defining a virtual electrode disposed between the first active electrode and the second active electrode. Additionally, the system may include a current source coupled to the implantable bio-stimulator device and configured to supply current to the first and second active electrodes in the implantable bio-stimulator array. In a further embodiment, the system includes an electrode controller coupled to the implantable bio-stimulator device, and configured to control operation of the implantable bio-stimulator device.

The system may also include one or more conductors coupling the first and second active electrodes to the electrode controller. The electrode controller may also include one or more driver circuits coupled to the first and second active electrodes, the driver circuit configured to supply current from the current source to the first and second active electrodes according to a timing sequence.

Methods of stimulating biological tissue are also presented. In one embodiment a method includes providing a stimulating current to a first active electrode in an implantable bio-stimulator device, and collecting return current from a second active electrode in the implantable bio-stimulator device. The first active electrode and the second active electrode may be arranged in an array configuration with one or more regions defining virtual electrodes disposed adjacent to the first active electrode and the second active electrode.

Additionally, the method may include providing the stimulating electrical charge in a pulse current pulse having finite pulse duration, the pulse duration sufficient to allow a portion of the electrical charge injected by the first electrode to accumulate in a region defining a virtual electrode. The region defining a virtual electrode may have one or more passive elements configured to steer the injected electrical charges to a predetermined position within the region defining the virtual electrode.

Additionally, the methods may include providing a plurality current waveforms to a plurality of active electrodes in an implantable array of bio-stimulator electrodes comprising both active electrodes and virtual electrodes, wherein the duration, timing, waveform, and firing sequences of the injected current is sufficient to generate a stimulation current in the virtual electrodes. A sequence of the waveforms may be applied to preselected active electrodes in the array of electrodes according to a predetermined pattern.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION

Various features and advantageous details are explained more fully with reference to the non-limiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure.

Figure 3:
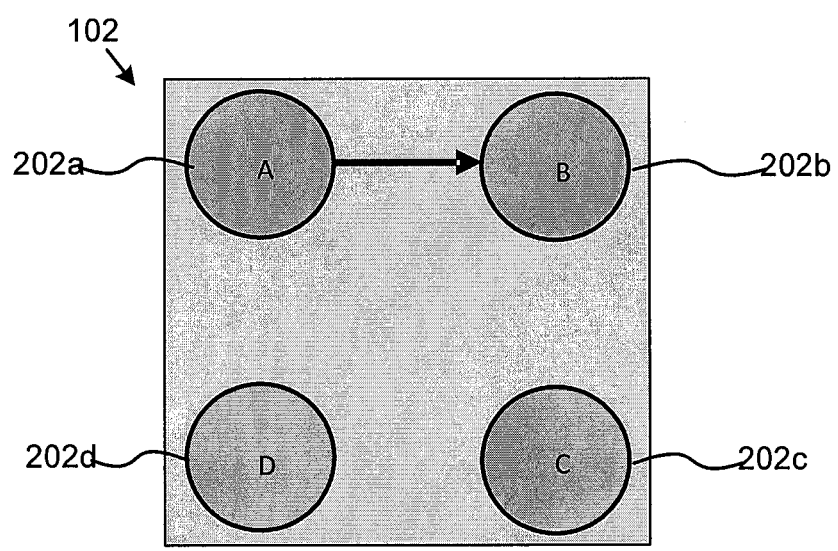
FIG. 3 is a logical diagram illustrating an embodiment of a stimulation current path.
Figure 4:
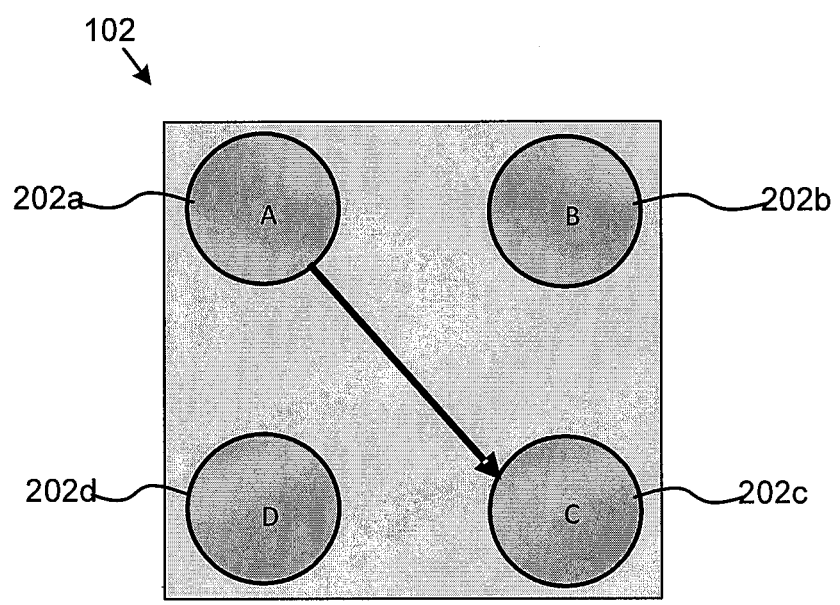
FIG. 4 is a logical diagram illustrating another embodiment of a stimulation current path.

FIGS. 3A-3B are logical diagrams illustrating embodiments of a stimulation current path. In FIG. 3, the external current return 204 is eliminated. For example, in the implantable electrode array 102 of FIG. 3, the electrodes 202a-d may be configured such that electrode 202a is coupled to a current source and electrode 202b is configured as a current return for current emitted by electrode 202a. Thus, a flow of current between electrode 202a and electrode 202b may be established. As described in the paragraphs to follow, a configuration in which a first electrode (e.g., 202a) is a current source and a second electrode (e.g., 202b) is a current return may be beneficial for controlling positioning of current density in tissue surrounding the electrodes (e.g., 202a-b) in the electrode array. FIG. 4 illustrates a second embodiment, wherein a diagonal current path is established between a first electrode (e.g., 202a) and a second electrode (e.g., 202c).

Figure 1:
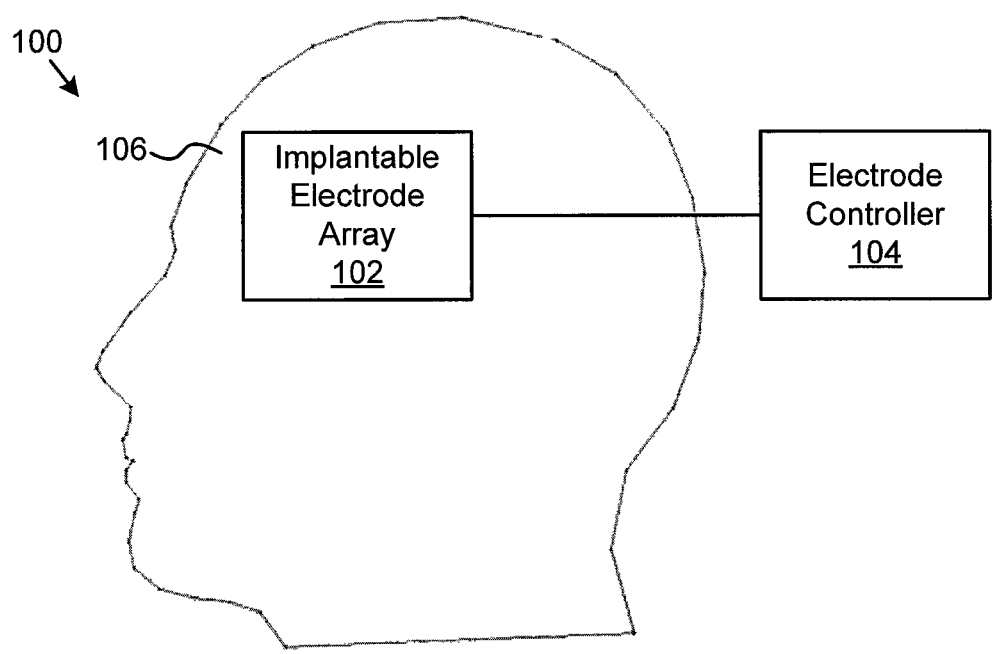
FIG. 1 is a schematic block diagram illustrating a system for biostimulation according to the prior art.
Figure 2:
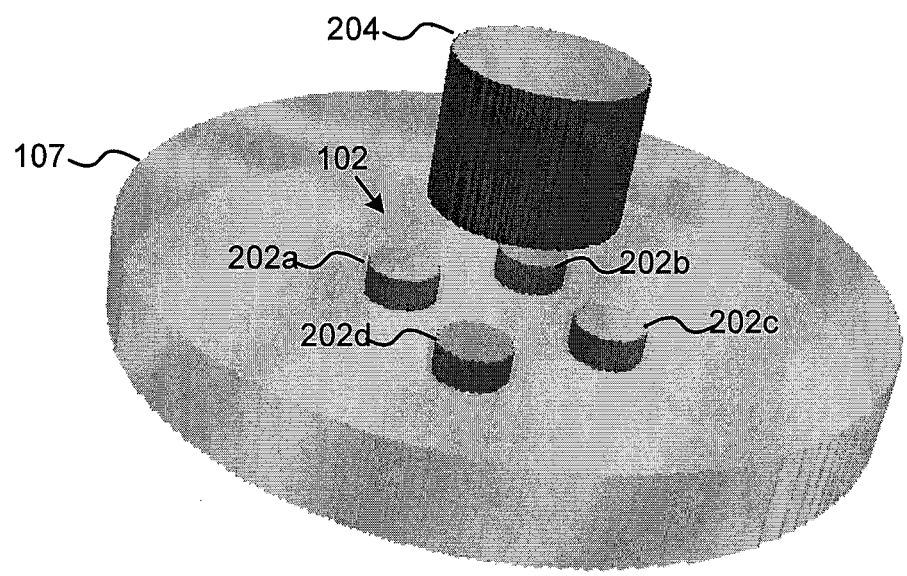
FIG. 2 is a perspective view diagram illustrating one embodiment of an implantable electrode array according to the prior art.

There are several distinctions that can be drawn from a comparison of the present embodiments with the prior art system of FIG. 2. For example, in the present embodiments, the active electrodes 202a-d are also configurable as current returns, where as in the prior art the current return 204 is not included as one of the elements of the electrode array 102. Indeed, it is the configurations in which the current is drawn between the electrodes in the array that helps facilitate distribution of charge to the virtual electrode discussed below with respect to FIG. 5. As illustrated in various embodiments herein, an current injection electrode (e.g., 102a) may situated in a coplanar orientation with the current return electrode (e.g., 102c). Indeed, because the current injection electrode and the current return electrode are part of a common electrode array 102, they may be formed on a common substrate.

Figure 5:
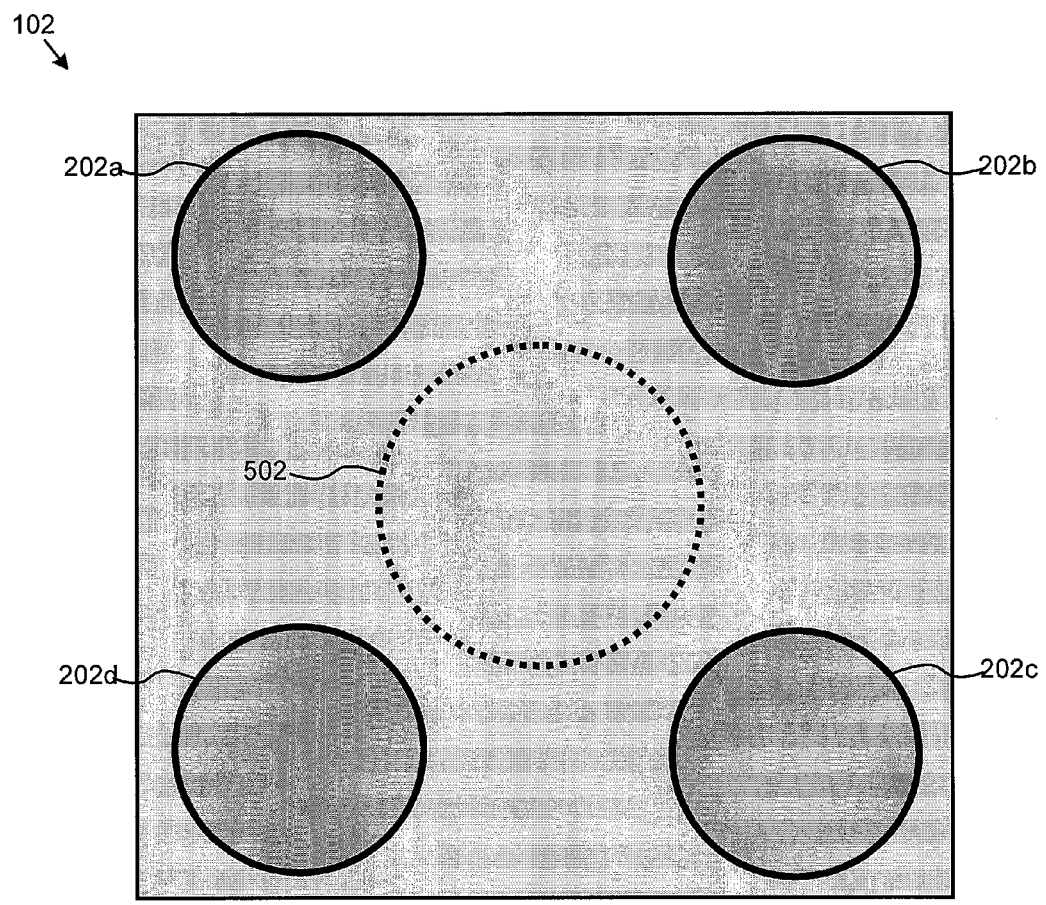
FIG. 5 is a schematic diagram illustrating one embodiment of an implantable electrode array having a virtual electrode.

FIG. 5 is a schematic diagram illustrating one embodiment of an implantable electrode array 102 having a virtual electrode 502. In one embodiment, the implantable electrode array 102 may include a plurality of electrodes 202a-d that are actively powered. The virtual electrode 502 may be passively powered by charge injection for the actively powered electrode 202a-d. For example, a current may be injected on a first electrode 202a for 0.1 μs and a second electrode 202c that is situated diagonally across from the first electrode 202a may be configured as a current collector for the current injected on the first electrode 202a. In such an embodiment, charge may flow through the virtual electrode region 502. In such an embodiment, charge may be rapidly injected from neighboring electrodes 202a-d using predetermined spatial and temporal patterns which are configured to increase the time-average amount of charge present in the area of the virtual electrode 502.

Figure 6:
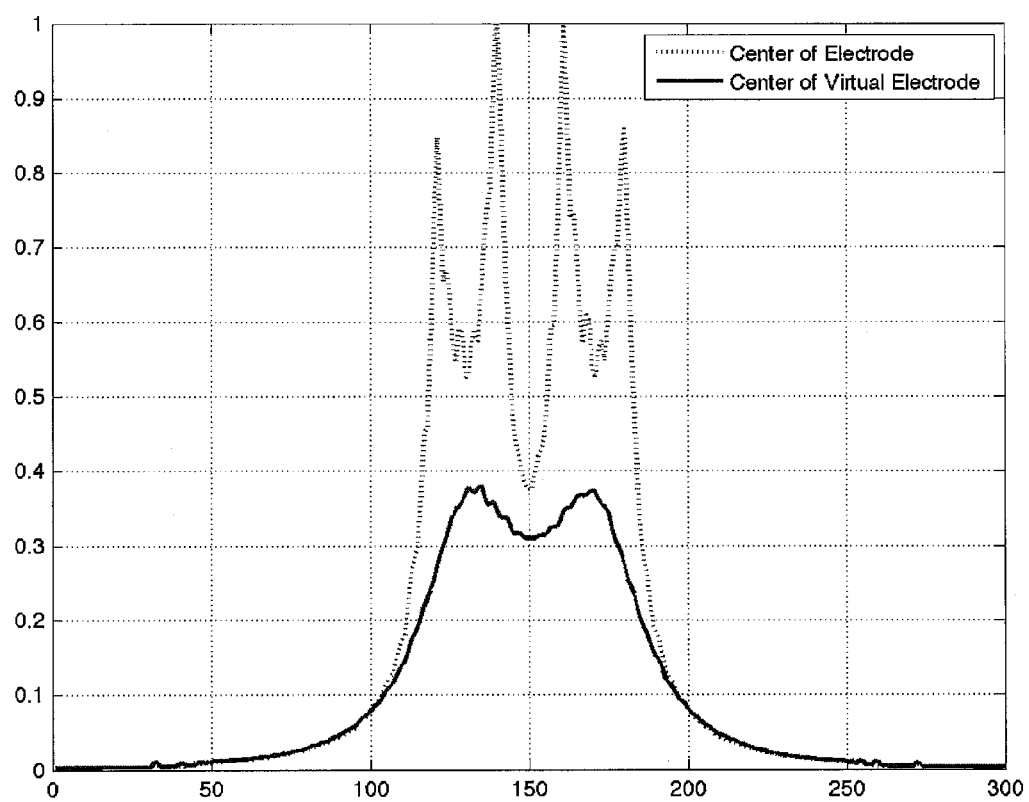
FIG. 6 is a graphical diagram illustrating a comparison of time-accumulated normalized current density magnitude across an active electrode and a virtual electrode in an embodiment that does not include a passive element.

FIG. 6 is a graphical diagram illustrating a comparison of accumulated normalized current density magnitude across an active electrode 202a-d and a virtual electrode 502 in an embodiment that does not include a passive element. As illustrated, there is some increase in the current density in the region corresponding to the virtual electrode, but the current density is still far lower than the current density at the center of the active electrodes 202a-d.

Figure 7:
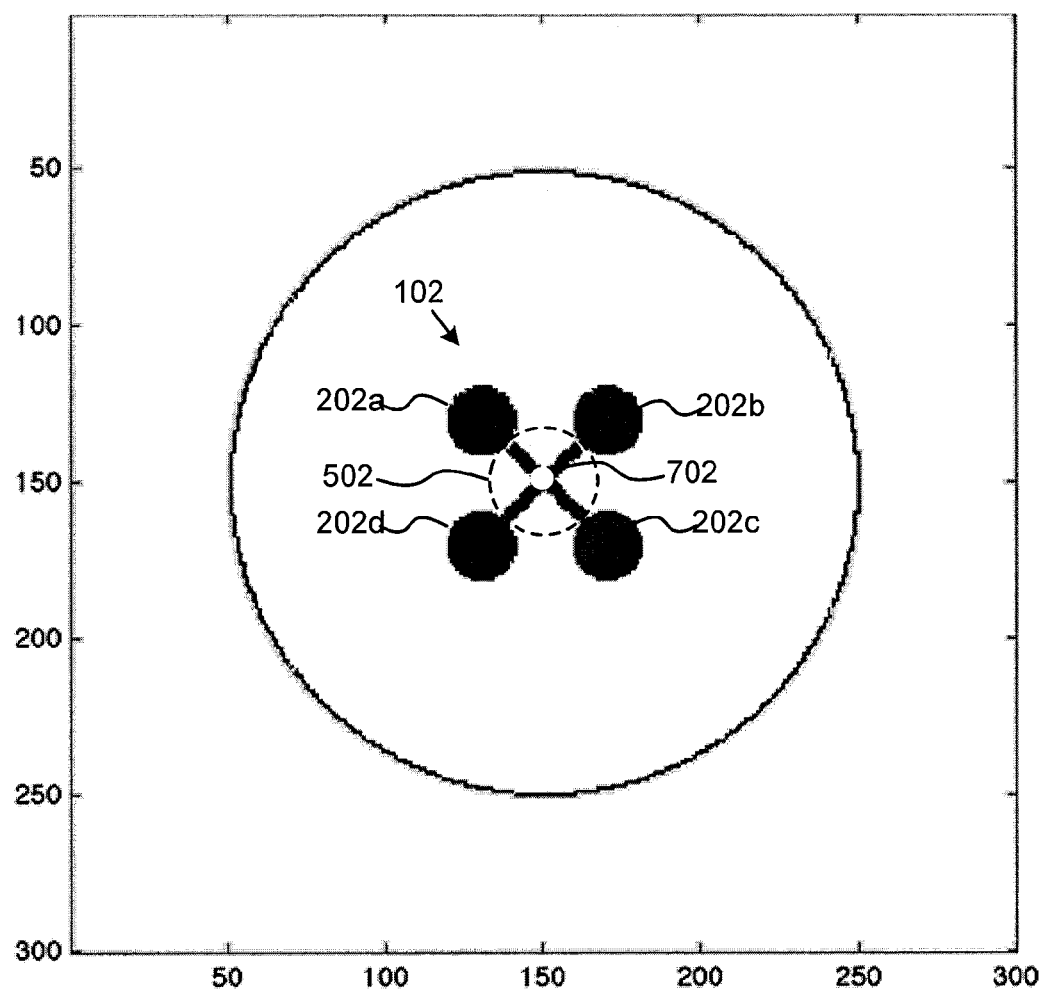
FIG. 7 is a schematic diagram illustrating one embodiment of an electrode array having passive elements.

FIG. 7 is a schematic diagram illustrating another embodiment of an electrode array 102 having one or more passive elements 702 comprising the virtual electrode 502. In this embodiment, the passive elements 702 may include a plurality of conductive arms positioned adjacent to the electrodes 202a-d. The passive elements 702 do not actually touch one another. The passive elements 702 may be formed of a biocompatible conductive material, such as gold, platinum, or other suitable conductive materials. In one embodiment, the passive elements 702 at least partially insulated from the electrodes 202a-d. Thus, in one embodiment, current density may accumulated on the passive electrodes 702, thereby creating a region of relatively higher charge density at the center point of the virtual electrode 502.

One benefit of including the passive elements 702 is that the passive elements 702 provide a low-resistance path between the current injection electrode (e.g., 102a) and the current return electrode (e.g., 102c). Thus, the charge will be more likely to follow a path along the passive elements 702 from the current injection electrode to the current return electrode. Accordingly, if the passive elements 702 are positioned in a region defining a virtual electrode 502, then the virtual electrode 502 will exhibit a higher current density than would be likely without the passive elements 702. FIGS. 9A-C illustrate this as well. Various geometries may be used to generate a variety of current density characteristics in the virtual electrode 502.

Figure 8A:
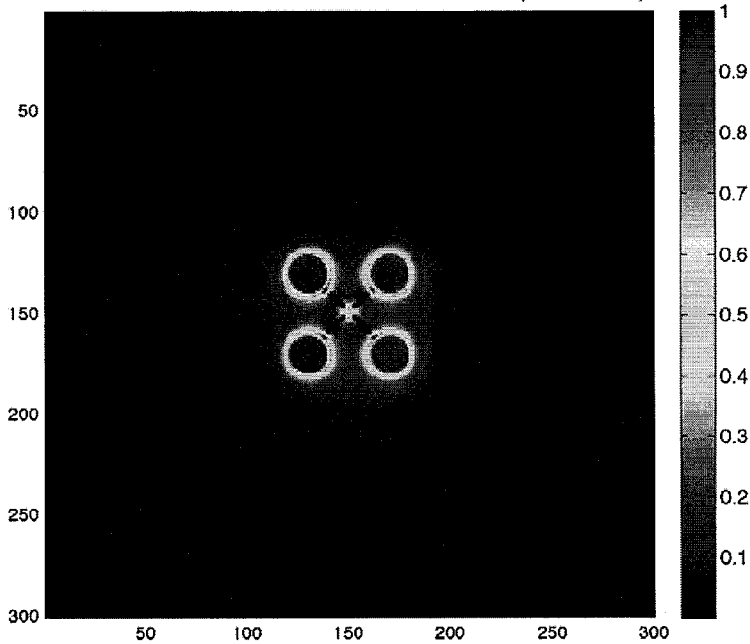
FIG. 8A is a graphical diagram illustrating a pattern of time-accumulated normalized current density at 10 μm from the embodiment of an implantable sensor array shown in FIG. 7.
Figure 8B:
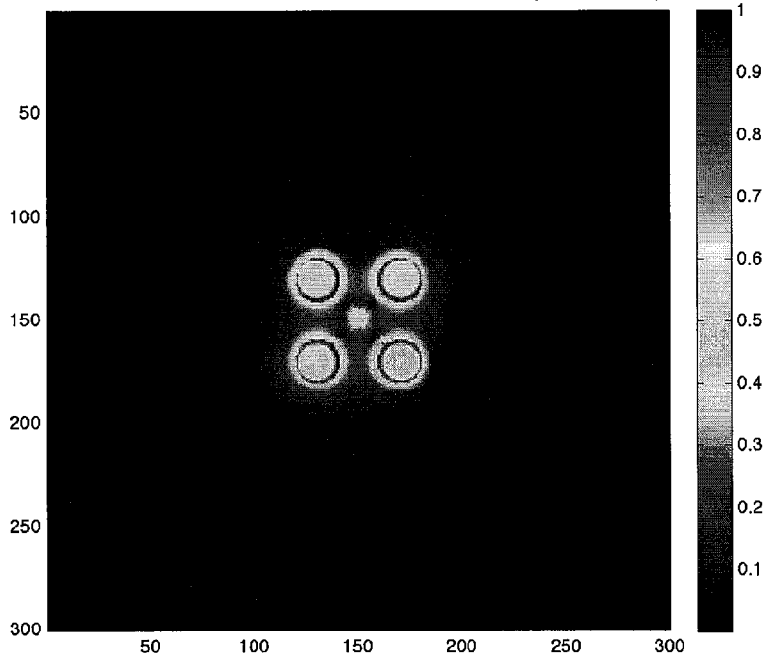
FIG. 8B is a graphical diagram illustrating a pattern of time-accumulated normalized current density at 30 μm from the embodiment of an implantable sensor array shown in FIG. 7.
Figure 8C:
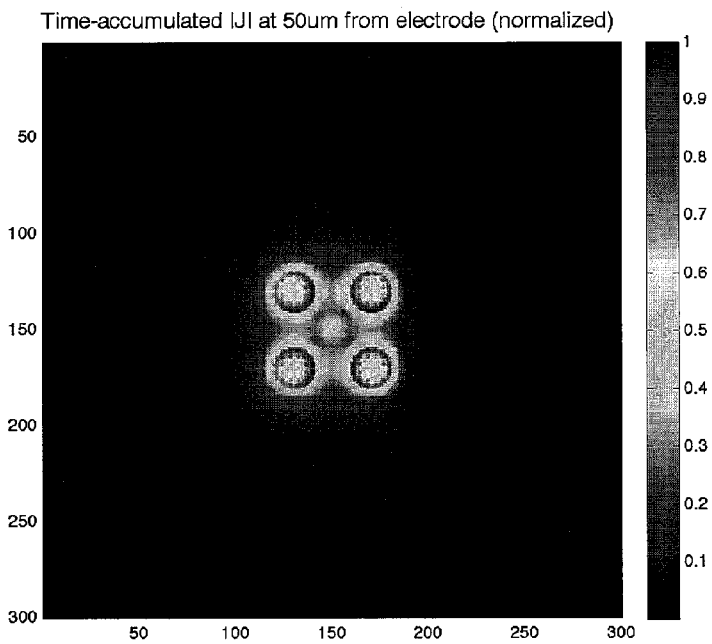
FIG. 8C is a graphical diagram illustrating a pattern of time-accumulated normalized current density at 50 μm from the embodiment of an implantable sensor array shown in FIG. 7.

FIG. 8A is a graphical diagram illustrating a pattern of accumulated normalized current density at 10 μm from the embodiment of an implantable sensor array 102 shown in FIG. 7. In this embodiment, a greater level of current density can be seen as the relatively light portions of FIG. 7. Although it appears that the greatest current density corresponds to the position of the active elements 202a-d, there does appear to be a higher current density concentration at the center of the virtual electrode 502 which is indicated by the lighter shaded portions in the middle of FIG. 8A. FIG. 8B is a graphical diagram illustrating a pattern of accumulated normalized current density at 30 μm from the embodiment of an implantable sensor array 102 and FIG. 8C is a graphical diagram illustrating a pattern of accumulated normalized current density at 50 μm from the implantable sensor array 102.

Figure 9:
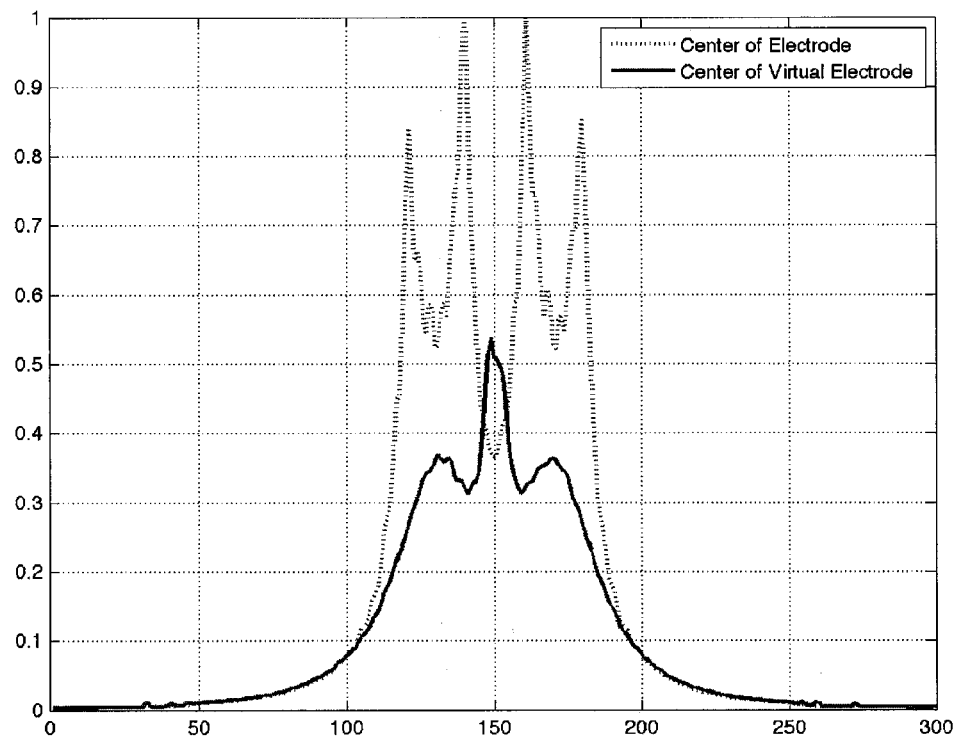
FIG. 9 is a graphical diagram illustrating a comparison of time-accumulated normalized current density magnitude across an active electrode and a virtual electrode in the embodiment of an implantable sensor array shown in FIG. 7.

FIG. 9 is a graphical diagram illustrating a comparison of accumulated normalized current density magnitude across an active electrode 202a-d and a virtual electrode 502 in the embodiment of an implantable sensor array 102 shown in FIG. 7. In this embodiment, a significant increase in the current density over the embodiment of FIG. 5 which did not include a passive element. Thus, it appears that in at least this "cross" configuration, the passive element facilitates collection of greater charge density at the center of the virtual electrode 502.

Figure 10:
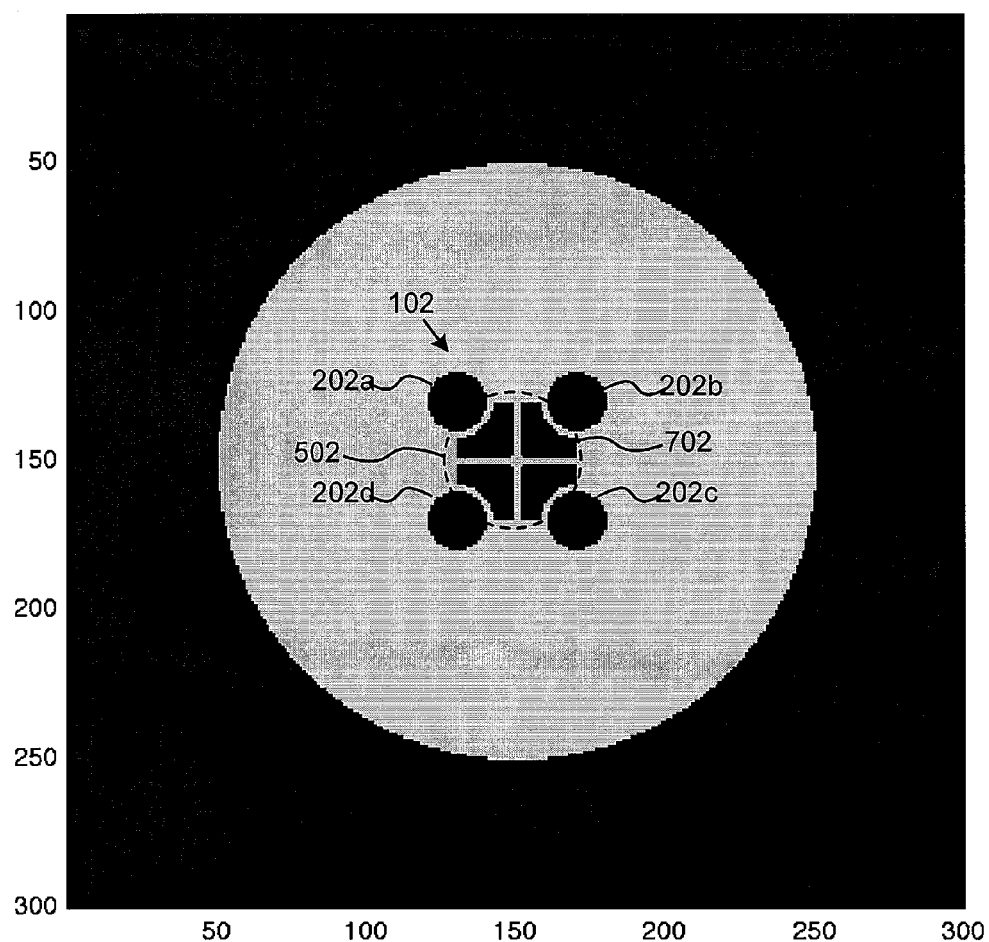
FIG. 10 is a schematic diagram illustrating another embodiment of an electrode array having passive elements.

FIG. 10 is a schematic diagram illustrating another embodiment of an electrode array 102 having passive elements 702. In this embodiment, the passive elements are configured to take up the majority of the area of the virtual electrode 502, leaving only a cross-shaped gap between the passive elements. Further, in this embodiment, the passive elements 702 are configured to match the contour of the active electrode 202a-d, thereby gaining greater electromagnetic coupling with the active electrodes 202a-d.

Figure 11A:
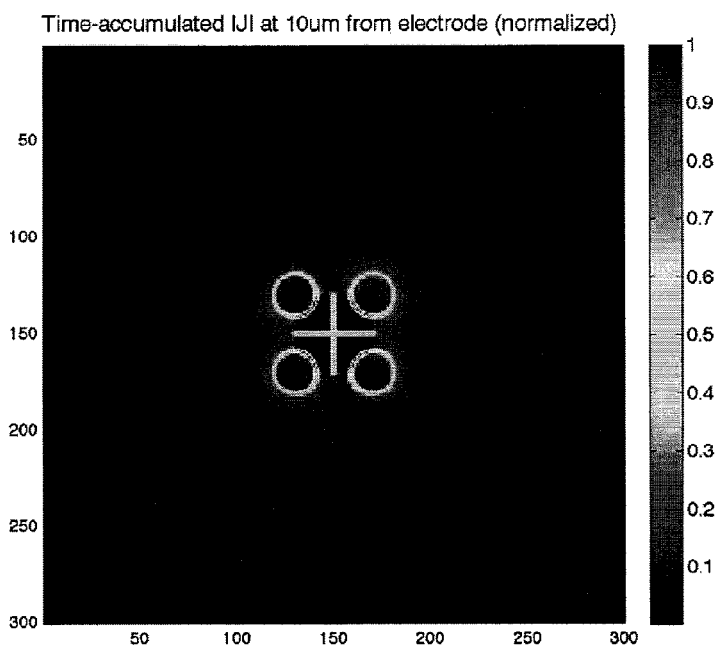
FIG. 11A is a graphical diagram illustrating a pattern of time-accumulated normalized current density at 10 μm from the embodiment of an implantable sensor array shown in FIG. 10.
Figure 11B:
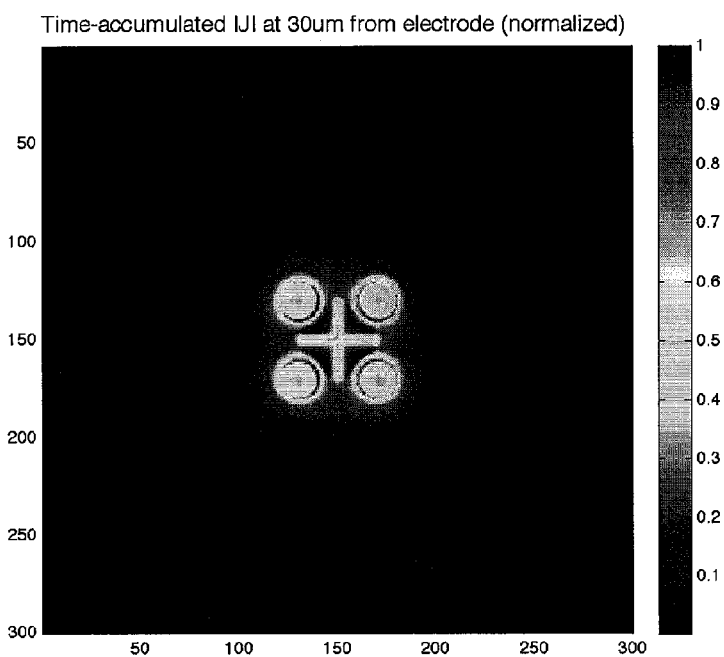
FIG. 11B is a graphical diagram illustrating a pattern of time-accumulated normalized current density at 30 μm from the embodiment of an implantable sensor array shown in FIG. 10.
Figure 11C:
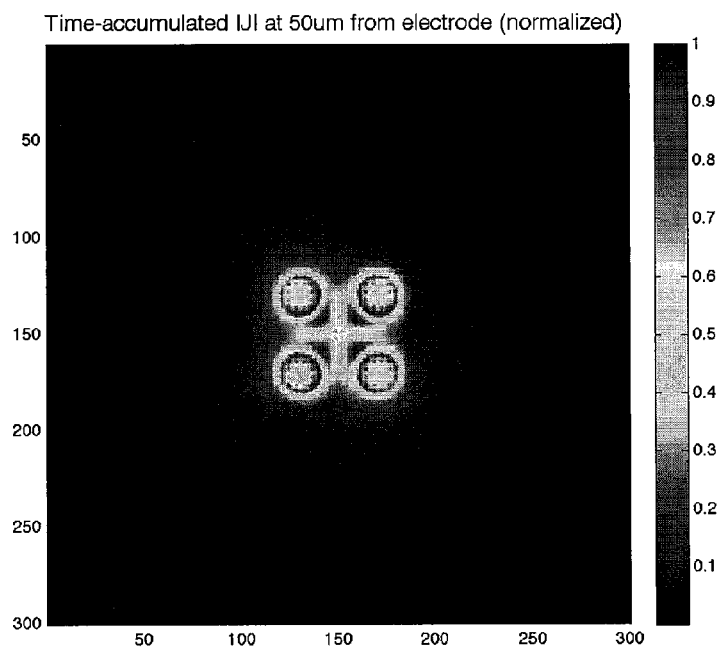
FIG. 11C is a graphical diagram illustrating a pattern of time-accumulated normalized current density at 50 μm from the embodiment of an implantable sensor array shown in FIG. 10.

FIG. 11A is a graphical diagram illustrating a pattern of accumulated normalized current density at 10 μm from the embodiment of an implantable sensor array 102 shown in FIG. 10. In this embodiment, it can be seen by the lighter cross-shaped portion in the center of the virtual electrode 502 that a relatively high level of current density is achievable than with the previously discussed embodiments. FIG. 11B is a graphical diagram illustrating a pattern of accumulated normalized current density at 30 μm and FIG. 11C is a graphical diagram illustrating a pattern of accumulated normalized current density at 50 μm. These show the highest current density at 50 μm.

Figure 12:
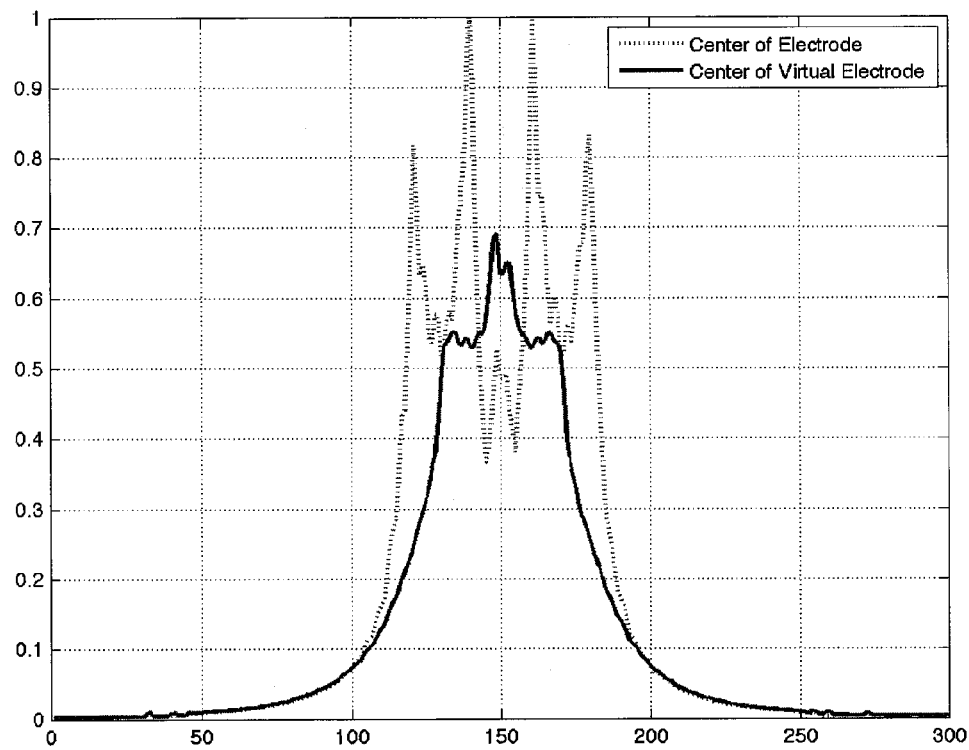
FIG. 12 is a graphical diagram illustrating a comparison of time-accumulated normalized current density magnitude across an active electrode and a virtual electrode in the embodiment of an implantable sensor array shown in FIG. 10.

FIG. 12 is a graphical diagram illustrating a comparison of accumulated normalized current density magnitude across an active electrode 202a-d and a virtual electrode 502 in the embodiment of an implantable sensor array 102 shown in FIG. 10. As can be seen from this graph, the current density achievable in the virtual electrode 502 is at or above the same level that is achievable in the active electrodes 202a-d. Thus, by tuning the size and geometry of the passive element, a variety of different current density levels and patters are achievable in the virtual electrode 502.

One of ordinary skill in the art will recognize other geometries for the passive elements 702 which may be suitable for various applications. For example, triangle shapes, star shapes, and other similar geometries may be used. In each case, one of ordinary skill in the art will appreciate that the current density in the region defining the virtual electrode 502 may be tuned by adjustment of the geometry including shape and size of the one or more passive elements 702.

Figure 13:
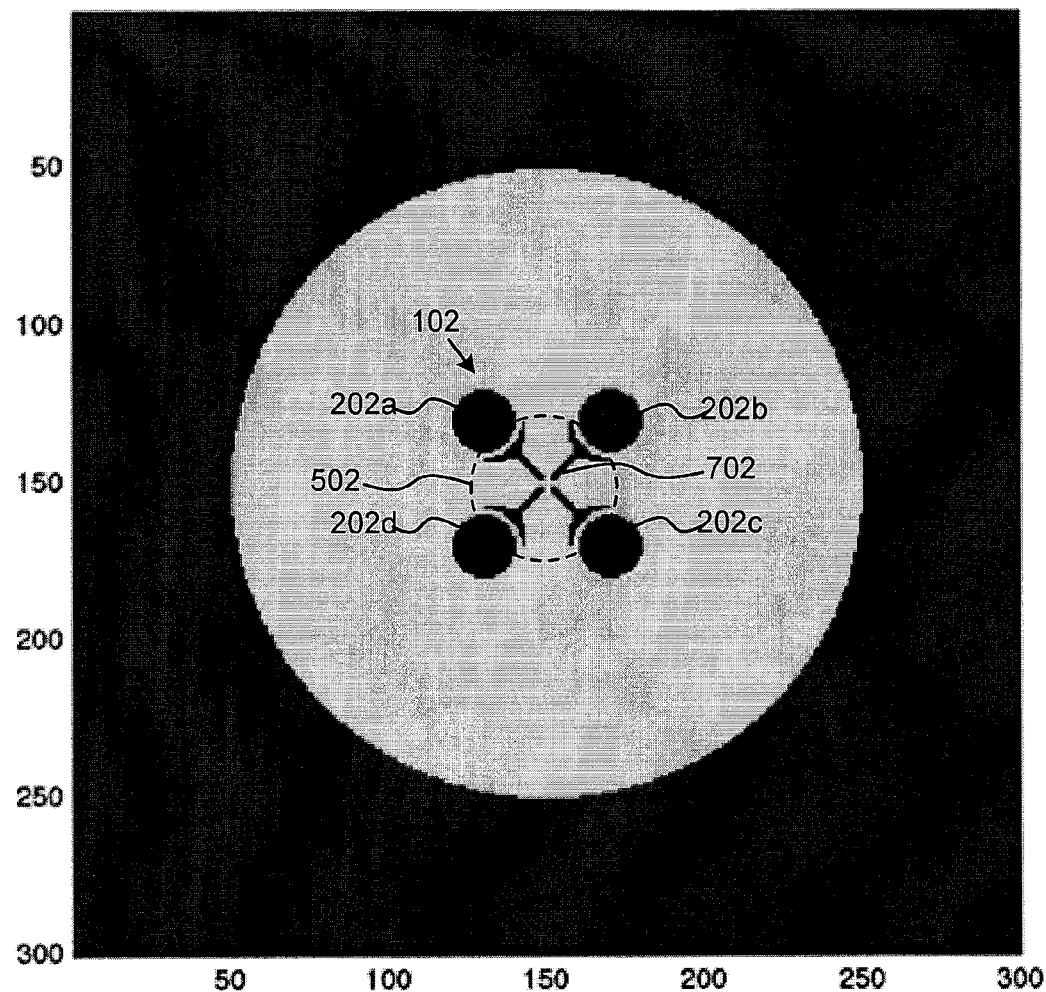
FIG. 13 is a schematic diagram illustrating another embodiment of an electrode array having passive elements.
Figure 14:
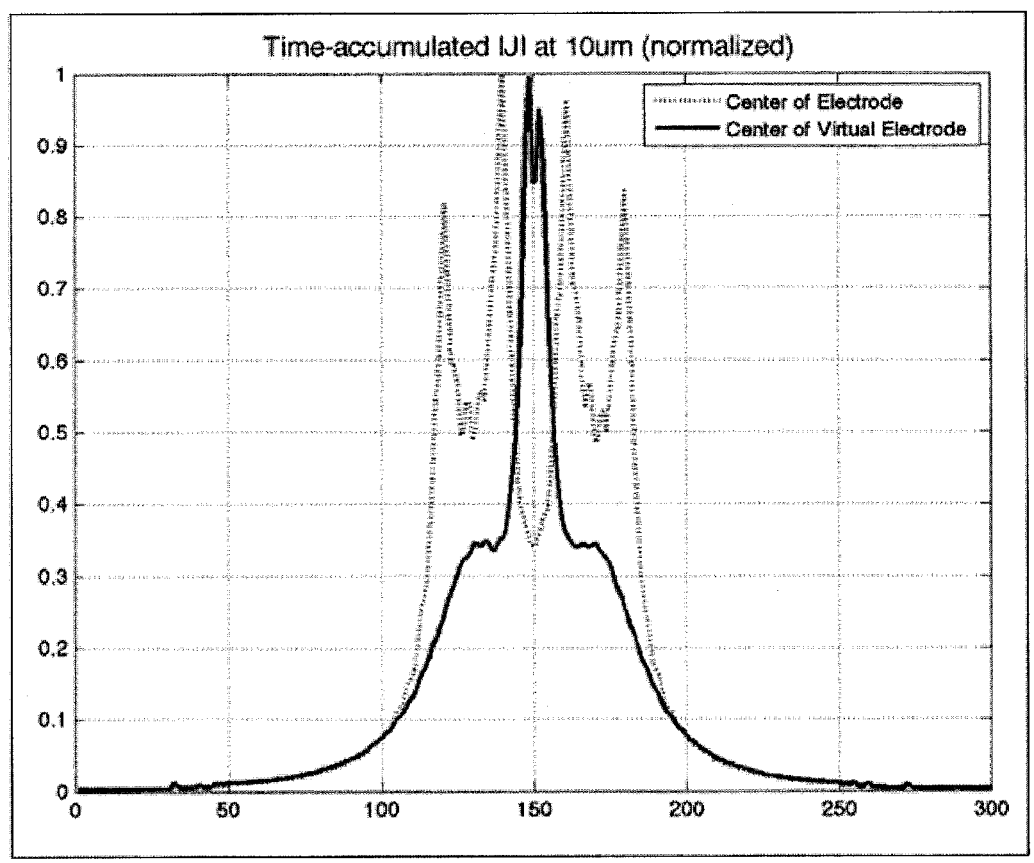
FIG. 14 is a graphical diagram illustrating a comparison of time-accumulated normalized current density magnitude across an active electrode and a virtual electrode in the embodiment of an implantable sensor array shown in FIG. 13.

FIG. 13 is a schematic diagram illustrating another embodiment of an electrode array 102 having passive elements 702. In the embodiment of FIG. 13, a region of the passive elements 702 adjacent to the active elements 202a-d is shaped to match a contour of the active elements 202a-d. In such an embodiment, a greater degree of electromagnetic coupling between the active elements 202a-d and the passive elements 702 may be achieved. For example, FIG. 14 is a graphical diagram illustrating a comparison of accumulated normalized current density magnitude across an active electrode and a virtual electrode in the embodiment of an implantable sensor array shown in FIG. 13.

Figure 15:
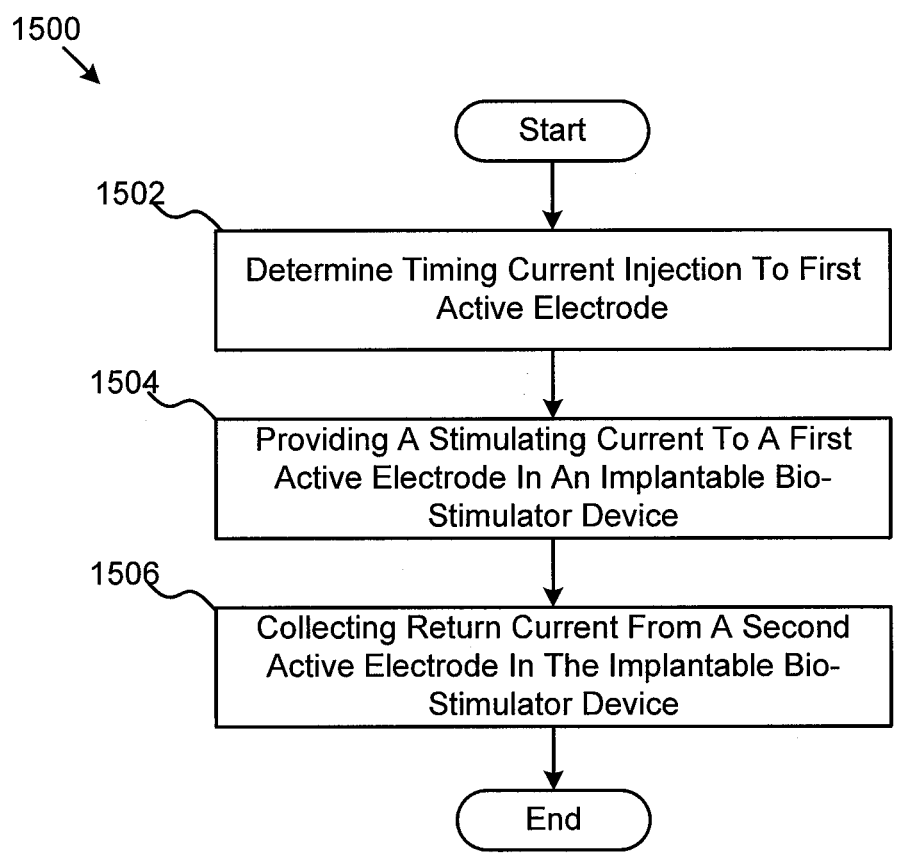
FIG. 15 is a schematic flowchart diagram illustrating one embodiment of a method of using an implantable electrode array having a virtual element.

FIG. 15 is a schematic flowchart diagram illustrating one embodiment of a method 1500 of using an implantable electrode array 102 having a virtual element 502. In one embodiment, a method 1500 includes providing 1504 a stimulating current to a first active electrode (e.g., 202a) in an implantable bio-stimulator device 102, and collecting 1506 return current from a second active electrode (e.g., 202c) in the implantable bio-stimulator device. The first active electrode 202a and the second active electrode 202c may be arranged in an array configuration 102 with one or more regions defining virtual electrodes 502 disposed adjacent to the first active electrode 202a and the second active electrode 202c.

Additionally, the method 1500 may include providing the stimulating current in a pulse current pulse having finite pulse duration, the pulse duration sufficient to allow a significant portion of the current emitted by the first electrode 202a to reach into a region defining a virtual electrode 502. The region defining a virtual electrode 502 may have one or more passive elements 702 configured to direct the current to a predetermined position within the region defining the virtual electrode 502.

Additionally, the methods 1500 may include providing a plurality of current pulses to a plurality of active electrodes 202a-d in an implantable array 102 of bio-stimulator electrodes comprising both active electrodes 202a-d and virtual electrodes 502, wherein a duration of the pulses is sufficient to generate a stimulation current in the virtual electrodes 502 as illustrated in FIGS. 6, 9, 12 and 14. A timing and/or sequence of the pulses may be applied to preselected 1502 active electrodes in the array 102 of electrodes according to a predetermined pattern.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An apparatus for stimulating biological tissue, the apparatus comprising:
an electrode array disposed on a substrate, including:
a first active electrode, disposed on the substrate, configured to receive a current from a current source;
a second active electrode, disposed on the substrate, configured to sink current emitted by the first active electrode; and
a virtual electrode defined by a region of the substrate disposed proximate to the first active electrode and the second active electrode and positioned such that the virtual electrode receives at least a portion of the current emitted by the first active electrode as the current emitted by the first active electrode is transferred between the first active electrode and the second active electrode, wherein at least the portion of the current is collected by the virtual electrode and has a current density sufficient to stimulate biological tissue proximate to the virtual electrode,
wherein the virtual electrode is configured to provide a stimulation point source for the biological tissue, thereby improving a resolution of the electrode array without increasing the electrode array complexity.

2. The apparatus of claim 1, wherein the region of the substrate defining the virtual electrode comprises one or more passive elements to increase the current density at a center point of the region defining the virtual electrode.

3. The apparatus of claim 2, wherein the passive elements comprise a conductive layer disposed on the region of the substrate defining the virtual electrode.

4. The apparatus of claim 2, wherein an electrical insulation barrier is disposed between the first and second active elements and the one or more passive elements.

5. The apparatus of claim 2, wherein the one or more passive elements are shaped in a pattern of a cross, a center point of the cross being disposed at the center point of the region defining the virtual electrode.

6. The apparatus of claim 2, wherein a majority portion of the region defining the virtual electrode comprises the one or more passive elements.

7. The apparatus of claim 2, wherein the one or more passive elements each comprise a portion adjacent to one of the plurality of active electrodes that is configured to match a contour of the active electrode.

8. The apparatus of claim 1, comprising a plurality of virtual electrodes and a plurality of active electrodes, the virtual electrodes positioned between the plurality of active electrodes in the array.

9. The apparatus of claim 1, wherein the virtual electrode is configured such that the current emitted by the first active electrode is rapidly collected by the virtual electrode using a predetermined spatial and temporal pattern, the spatial and temporal pattern configured to increase the time-average amount of current present in the virtual electrode.

10. A system for stimulating biological tissue comprising:
   a current source configured to supply a current;
   an implantable bio-stimulator device, disposed on a substrate, coupled to the current source, the implantable bio-stimulator device comprising:
      a first active electrode, disposed on the substrate, configured to receive a current from the current source;
      a second active electrode, disposed on the substrate, configured to return current emitted by the first active electrode to ground; and
      a virtual electrode defined by a region of the substrate disposed proximate to the first active electrode and the second active electrode and positioned such that the virtual electrode receives at least a portion of the current emitted by the first active electrode as the current emitted by the first active electrode is transferred between the first active electrode and the second active electrode, wherein at least the portion of the current is collected by the virtual electrode and has a current density sufficient to stimulate biological tissue proximate to the virtual electrode,
   wherein the virtual electrode is configured to provide a stimulation point source for the biological tissue, thereby improving a resolution of the electrode array without increasing the electrode array complexity.

11. The system of claim 10, further comprising an electrode controller coupled to the implantable bio-stimulator device, and configured to control operation of the implantable bio-stimulator device.

12. The system of claim 11, further comprising one or more conductors coupling the first and second active electrodes to the electrode controller.

13. The system of claim 11, wherein the electrode controller comprises one or more driver circuits coupled to the first and second active electrodes, the driver circuit configured to supply the current from the current source to the first and second active electrodes according to a timing sequence.

14. The system of claim 10, wherein the virtual electrode is configured such that the current emitted by the first active electrode is rapidly collected by the virtual electrode using a predetermined spatial and temporal pattern, the spatial and temporal pattern configured to increase the time-average amount of current present in the virtual electrode.

* * * * *